United States Patent
Chang

(10) Patent No.: US 12,414,770 B2
(45) Date of Patent: Sep. 16, 2025

(54) ARTICULATION ASSEMBLY FOR A SURGICAL DEVICE

(71) Applicant: Covidien LP, Mansfield, MA (US)

(72) Inventor: Lan Chang, Shanghai (CN)

(73) Assignee: Covidien LP, Mansfield, MA (US)

( * ) Notice: Subject to any disclaimer, the term of this patent is extended or adjusted under 35 U.S.C. 154(b) by 6 days.

(21) Appl. No.: 18/562,392

(22) PCT Filed: May 21, 2021

(86) PCT No.: PCT/CN2021/095023
§ 371 (c)(1),
(2) Date: Nov. 20, 2023

(87) PCT Pub. No.: WO2022/241744
PCT Pub. Date: Nov. 24, 2022

(65) Prior Publication Data
US 2024/0252169 A1 Aug. 1, 2024

(51) Int. Cl.
*A61B 17/072* (2006.01)
*F16C 11/10* (2006.01)
(Continued)

(52) U.S. Cl.
CPC ........ *A61B 17/07207* (2013.01); *F16C 11/10* (2013.01); *A61B 2017/00367* (2013.01);
(Continued)

(58) Field of Classification Search
CPC .... A61B 17/07207; A61B 2017/00367; A61B 2017/07257; A61B 2017/07271; A61B 2017/2927; F16C 11/10
(Continued)

(56) References Cited

U.S. PATENT DOCUMENTS 3,499,591 A 3/1970 Green
3,777,538 A 12/1973 Weatherly et al.
(Continued)

FOREIGN PATENT DOCUMENTS

AU 198654765 9/1986
CA 2773414 A1 11/2012
(Continued)

OTHER PUBLICATIONS

International Search Report for Application No. PCT/CN2021/095023 dated Feb. 16, 2022.
(Continued)

*Primary Examiner* — Michelle Lopez

(57) ABSTRACT

A surgical device includes an elongate body, a tool assembly supported on the elongate body for articulation, and an articulating mechanism for selectively articulating the tool assembly in relation to the elongate body. The articulation mechanism includes an articulation lever and a pair of locking assemblies. The articulation lever is movable to articulate the tool assembly in relation to the elongate body about an articulation axis. The locking assemblies are configured to prevent movement of the articulation lever until one of the locking assemblies is moved from a locked position to an unlocked position. The locking assemblies are movable from their locked positions to their unlocked positions prior to movement of the articulation lever to reduce the force required to manipulate the articulation lever and to facilitate articulation in continuous fashion.

16 Claims, 11 Drawing Sheets

(51) Int. Cl.
    *A61B 17/00*     (2006.01)
    *A61B 17/29*     (2006.01)
(52) U.S. Cl.
    CPC ............... *A61B 2017/07257* (2013.01); *A61B 2017/07271* (2013.01); *A61B 2017/2927* (2013.01)
(58) Field of Classification Search
    USPC ..................................................... 227/176.1
    See application file for complete search history.

(56) References Cited

U.S. PATENT DOCUMENTS

| | | |
|---|---|---|
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |

(56) References Cited

U.S. PATENT DOCUMENTS

| | | | |
|---|---|---|---|
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A * | 10/1998 | Huitema .......... A61B 17/07207 74/528 |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |

(56) References Cited

U.S. PATENT DOCUMENTS

| | | |
|---|---|---|
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |

(56) References Cited

U.S. PATENT DOCUMENTS

| | | |
|---|---|---|
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |

(56) References Cited

U.S. PATENT DOCUMENTS

| | | |
|---|---|---|
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |

(56) References Cited

U.S. PATENT DOCUMENTS

| | | | |
|---|---|---|---|
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |

(56) References Cited

U.S. PATENT DOCUMENTS

| | | |
|---|---|---|
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,533 B2 | 6/2014 | Whitman |
| 8,746,534 B2 | 6/2014 | Farascioni |
| 8,746,535 B2 | 6/2014 | Shelton, IV et al. |
| 8,747,421 B2 | 6/2014 | Balbierz et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,960,520 B2 | 2/2015 | McCuen |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,979,827 B2 * | 3/2015 | Cappola ........... A61B 17/07207 606/1 |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,017,371 B2 | 4/2015 | Whitman et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |

(56) References Cited

U.S. PATENT DOCUMENTS

| | | |
|---|---|---|
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,693,815 B2 | 7/2017 | Motai |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,092 B2 | 8/2017 | Baxter, III et al. |
| 9,724,095 B2 | 8/2017 | Gupta et al. |
| 9,757,128 B2 | 9/2017 | Baber et al. |
| 9,763,662 B2 | 9/2017 | Shelton, IV et al. |
| 9,770,245 B2 | 9/2017 | Swayze et al. |
| 9,775,610 B2 | 10/2017 | Nicholas et al. |
| 9,775,635 B2 | 10/2017 | Takei |

(56) References Cited

U.S. PATENT DOCUMENTS

| | | |
|---|---|---|
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter, III et al. |
| 9,855,038 B2 | 1/2018 | Smith et al. |
| 9,855,040 B2 | 1/2018 | Kostrzewski |
| 9,861,358 B2 | 1/2018 | Marczyk et al. |
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |
| 9,913,646 B2 | 3/2018 | Shelton, IV |
| 9,918,714 B2 | 3/2018 | Gibbons, Jr. |
| 9,918,717 B2 | 3/2018 | Czernik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,750 B2 | 10/2018 | Zergiebel et al. |
| 10,092,290 B2 | 10/2018 | Yigit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,285,700 B2 | 5/2019 | Scheib |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,937 B2 * | 7/2019 | Williams .......... A61B 17/07207 |
| 10,349,939 B2 | 7/2019 | Shelton, IV et al. |
| 10,349,941 B2 | 7/2019 | Marczyk et al. |
| 10,368,867 B2 | 8/2019 | Harris et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,610,224 B2 | 4/2020 | Shelton, IV et al. |
| 10,617,412 B2 | 4/2020 | Shelton, IV et al. |
| 10,624,634 B2 | 4/2020 | Shelton, IV et al. |
| 10,675,026 B2 | 6/2020 | Harris et al. |
| 10,687,806 B2 | 6/2020 | Shelton, IV et al. |
| 10,695,053 B2 | 6/2020 | Hess et al. |
| 10,729,434 B2 | 8/2020 | Harris et al. |
| 10,765,424 B2 | 9/2020 | Baxter, III et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 10,905,420 B2 | 2/2021 | Jasemian et al. |
| 10,905,422 B2 | 2/2021 | Bakos et al. |
| 10,959,726 B2 | 3/2021 | Williams et al. |
| 11,064,999 B2 | 7/2021 | Nelson et al. |
| 11,090,051 B2 | 8/2021 | Kostrzewski |
| 11,207,065 B2 | 12/2021 | Harris et al. |
| 11,213,294 B2 | 1/2022 | Shelton, IV et al. |
| 11,266,409 B2 | 3/2022 | Huitema et al. |
| 11,278,288 B2 | 3/2022 | Rector et al. |
| 11,439,391 B2 | 9/2022 | Bruns et al. |
| 11,564,684 B2 | 1/2023 | Harris et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |

(56) References Cited

U.S. PATENT DOCUMENTS

| | | |
|---|---|---|
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0065604 A1 | 3/2010 | Weng |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0147433 A1 | 6/2011 | Shelton, IV et al. |
| 2011/0163146 A1 | 7/2011 | Ortiz et al. |
| 2011/0192882 A1 | 8/2011 | Hess et al. |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0168484 A1 | 7/2012 | Scirica et al. |
| 2012/0193394 A1 | 8/2012 | Holcomb et al. |
| 2012/0193399 A1 | 8/2012 | Holcomb et al. |
| 2012/0199629 A1 | 8/2012 | Cappola et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0241504 A1 | 9/2012 | Soltz et al. |
| 2012/0248169 A1 | 10/2012 | Widenhouse et al. |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041406 A1 | 2/2013 | Bear et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0098970 A1 | 4/2013 | Racenet et al. |
| 2013/0153641 A1 | 6/2013 | Shelton, IV et al. |
| 2013/0175316 A1 | 7/2013 | Thompson et al. |
| 2013/0245676 A1* | 9/2013 | Cappola ........... A61B 17/07207 606/213 |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0048580 A1 | 2/2014 | Merchant et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175150 A1 | 6/2014 | Shelton, IV et al. |
| 2014/0239047 A1 | 8/2014 | Hodgkinson et al. |
| 2014/0246475 A1 | 9/2014 | Hall et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0367445 A1 | 12/2014 | Ingmanson et al. |
| 2015/0076211 A1 | 3/2015 | Irka et al. |
| 2015/0134076 A1 | 5/2015 | Shelton, IV et al. |
| 2015/0173749 A1 | 6/2015 | Shelton, IV et al. |
| 2015/0173756 A1 | 6/2015 | Baxter, III et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1 | 10/2015 | Huitema et al. |
| 2015/0374372 A1 | 12/2015 | Zergiebel et al. |
| 2016/0166249 A1 | 6/2016 | Knodel |
| 2016/0166253 A1 | 6/2016 | Knodel |
| 2016/0235494 A1 | 8/2016 | Shelton, IV et al. |
| 2016/0302791 A1 | 10/2016 | Schmitt |
| 2016/0302817 A1 | 10/2016 | Worrell et al. |
| 2016/0354176 A1 | 12/2016 | Schmitt |
| 2017/0000483 A1 | 1/2017 | Motai et al. |
| 2017/0340327 A1 | 11/2017 | Yang et al. |
| 2021/0077102 A1 | 3/2021 | Williams |
| 2021/0177406 A1* | 6/2021 | Nicholas ........... A61B 17/07207 |

FOREIGN PATENT DOCUMENTS

| | | |
|---|---|---|
| CA | 2884962 A1 | 11/2015 |
| CN | 101396294 B | 4/2012 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |

(56) References Cited

FOREIGN PATENT DOCUMENTS

| | | |
|---|---|---|
| EP | 0539762 A1 | 5/1993 |
| EP | 0541950 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2484290 B1 | 7/2015 |
| EP | 2907456 A1 | 8/2015 |
| EP | 3138509 A1 | 3/2017 |
| EP | 3338660 A1 | 6/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2013215572 A | 10/2013 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 2015191887 A1 | 12/2015 |
| WO | 2018161313 A1 | 9/2018 |
| WO | 2019186434 A1 | 10/2019 |

OTHER PUBLICATIONS

Written Opinion for Application No. PCT/CN2021/095023 dated Feb. 16, 2022.
European Search Report for EP Application No. 21 94 0196 mailed Jan. 8, 2025 (9 pages).

* cited by examiner

ARTICULATION ASSEMBLY FOR A SURGICAL DEVICE

FIELD

This disclosure is generally related to surgical devices for endoscopic use and, more particularly, to surgical devices including articulation mechanisms for articulating tool assemblies.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

During laparoscopic or endoscopic surgical procedures, access to a surgical site is achieved through a small incision or through a narrow cannula inserted through a small entrance wounds in a patient. Because of limited area available to access the surgical site, many endoscopic devices include mechanisms for articulating the tool assembly of the device in relation to a body portion of the device about a pivot axis.

Typically, articulation mechanisms for articulating a tool assembly of a surgical stapling device include a lever that can be manipulated to articulate the tool assembly. To manipulate the lever, the force of a biasing member must be overcome. This increases the forces required to articulate the tool assembly.

A continuing need exists in the art for an articulating mechanism that can be operated with minimal force.

SUMMARY

This disclosure is directed to a surgical stapling device including a tool assembly, an elongate body, and an articulation mechanism having an articulation lever and a pair of locking assemblies. The articulation lever is movable to articulate the tool assembly in relation to the elongate body about an articulation axis that is transverse to a longitudinal axis of the elongate body. The locking assemblies are configured to prevent movement of the articulation lever until one of the locking assemblies is moved from a locked position to an unlocked position. The locking assemblies are movable from their locked positions to their unlocked positions prior to movement of the articulation lever to reduce the force required to manipulate the articulation lever and to facilitate articulation in continuous fashion.

Aspects of the disclosure are directed to an articulation assembly for use with a surgical device that includes a housing, an articulation lever, a first ratchet, a second ratchet, a drive member, an articulation link, a first locking assembly, and a second locking assembly. The housing defines a circular bore and a cavity and includes a base wall separating the circular bore from the cavity. The base wall defines an opening that communicates the circular bore with the cavity. The articulation lever is rotatably supported in relation to the circular bore. The first ratchet has an annular array of teeth supported within the circular bore. The second ratchet has an annular array of teeth positioned adjacent the first ratchet. The drive member includes a shaft having a first end coupled to the articulation lever and a second end. The shaft extends through the opening in the base wall of the housing. The drive member is rotatable in response to rotation of the articulation lever. The articulation link is coupled to the second end of the drive member such that rotation of the drive member causes longitudinal movement of the articulation link. The first locking assembly is supported on the articulation lever and includes a first locking member that is movable from a first position engaged with the first ratchet to a second position disengaged with the first ratchet. The first locking member is configured to prevent rotation of the articulation lever in a counterclockwise direction when the first locking member is in its first position. The second locking assembly is supported on the articulation lever and includes a second locking member that is movable from a first position engaged with the second ratchet to a second position disengaged with the second ratchet. The second locking member is configured to prevent rotation of the articulation lever in a clockwise direction when the second locking member is in its first position.

In aspects of the disclosure, the first locking assembly includes a first actuator that is supported on the articulation lever, and the second locking assembly includes a second actuator that is supported on the articulation lever.

In some aspects of the disclosure, the first actuator is movable to move the first locking member from its first position to its second position and the second actuator is movable to move the second locking member from its first position to its second position.

In certain aspects of the disclosure, the first locking assembly includes a first slider that is positioned between the first actuator and the first locking member, and the second locking assembly includes a second slider that is positioned between the second actuator and the second locking member.

In aspects of the disclosure, the first actuator is movable from a first position to a second position to move the first slider from a first position to a second position into engagement with the first locking member to move the first locking member from its first to its second position, and the second actuator is movable from a first position to a second position to move the second slider from a first position to a second position into engagement with the second locking member to move the second locking member from its first position to its second position.

In some aspects of the disclosure, the first actuator and the first slider include abutting cam surfaces such that transverse movement of the first actuator causes longitudinal movement of the first slider.

In certain aspects of the disclosure, the second actuator and the second slider include abutting cam surfaces such that transverse movement of the second actuator causes longitudinal movement of the second slider.

In aspects of the disclosure, the articulation assembly includes a biasing member that is positioned to urge the first and second actuators towards their first positions.

In some aspects of the disclosure, the first and second locking members are formed of a resilient material.

In certain aspects of the disclosure, the first locking member includes a first retention portion and a first ratchet finger, and the second locking member includes a second retention portion and a second ratchet finger.

In aspects of the disclosure, the first ratchet finger is engaged with the first ratchet when the first locking member is in its first position and the second ratchet finger is engaged with the second ratchet when the second locking member is in its first position.

In some aspects of the disclosure, the articulation assembly includes a first biasing member positioned to urge the first slider to its first position and a second biasing member positioned to urge the second slider to its first position.

In certain aspects of the disclosure, the second end of the drive member includes a disc-shaped member, and the articulation assembly includes a cam member and a coupling member.

In aspects of the disclosure, the cam member is supported on the disc-shaped member and coupled to the coupling member such that rotational movement of the drive member causes longitudinal movement of the coupling member.

In aspects of the disclosure, the coupling member is coupled to the articulation link such that longitudinal movement of the coupling member causes longitudinal movement of the articulation link.

In aspects of the disclosure, the tool assembly includes an anvil and a cartridge assembly.

Other aspects of the disclosure are directed to a surgical device that includes an elongate body, a tool assembly, and an articulation assembly. The elongate body defines a first longitudinal axis and has a proximal portion and a distal portion. The tool assembly defines a second longitudinal axis and is pivotably supported on the distal portion of the elongate body by a pivot member. The pivot member defines an articulation axis that is transverse to the first longitudinal axis. The tool assembly is pivotable about the articulation axis in relation to the elongate body between an articulated position in which the first and second longitudinal axes are coaxial and articulated positions in which the first and second longitudinal axes are misaligned. The articulation assembly includes a housing, an articulation lever, a first ratchet, a second ratchet, a drive member, an articulation link, a first locking assembly, and a second locking assembly. The housing defines a circular bore and a cavity and includes a base wall separating the circular bore from the cavity. The base wall defines an opening that communicates the circular bore with the cavity. The articulation lever is rotatably supported in relation to the circular bore. The first ratchet has an annular array of teeth supported within the circular bore. The second ratchet has an annular array of teeth supported adjacent the first ratchet. The drive member includes a shaft having a first end coupled to the articulation lever and a second end. The shaft extends through the opening in the base wall of the housing, and the drive member is rotatable in response to rotation of the articulation lever. The articulation link has a proximal portion and a distal portion. The proximal portion is coupled to the second end of the drive member such that rotation of the drive member causes longitudinal movement of the articulation link. The distal portion of the articulation link is coupled to the tool assembly such that longitudinal movement of the articulation link causes the tool assembly to move between the non-articulated and articulated positions. The first locking assembly is supported on the articulation lever and includes a first locking member that is movable from a first position engaged with the first ratchet to a second position disengaged with the first ratchet. The first locking member is configured to prevent rotation of the articulation lever in a counterclockwise direction when the first locking member is in its first position. The second locking assembly is supported on the articulation lever and includes a second locking member that is movable from a first position engaged with the second ratchet to a second position disengaged with the second ratchet. The second locking member is configured to prevent rotation of the articulation lever in a clockwise direction when the second locking member is in its first position.

Other aspects of the disclosure are directed to an articulation assembly for use with a surgical device that includes a housing, an articulation lever, a first ratchet, a second ratchet, a drive member, a first locking assembly, and a second locking assembly. The housing defines a circular bore. The articulation lever is rotatably supported in relation to the circular bore. The first ratchet has an annular array of teeth supported on the housing. The second ratchet has an annular array of teeth positioned adjacent the first ratchet. The drive member includes a shaft having a first end coupled to the articulation lever. The first locking assembly is supported on the articulation lever and includes a first locking member that is movable from a first position engaged with the first ratchet to a second position disengaged with the first ratchet. The first locking member is configured to prevent rotation of the articulation lever in a counterclockwise direction when the first locking member is in its first position. The second locking assembly is supported on the articulation lever and includes a second locking member that is movable from a first position engaged with the second ratchet to a second position disengaged with the second ratchet. The second locking member is configured to prevent rotation of the articulation lever in a clockwise direction when the second locking member is in its first position.

Other features of the disclosure will be appreciated from the following description.

BRIEF DESCRIPTION OF DRAWINGS

Various aspects of this disclosure are described herein below with reference to the drawings, wherein.

DETAILED DESCRIPTION

Figure 1:
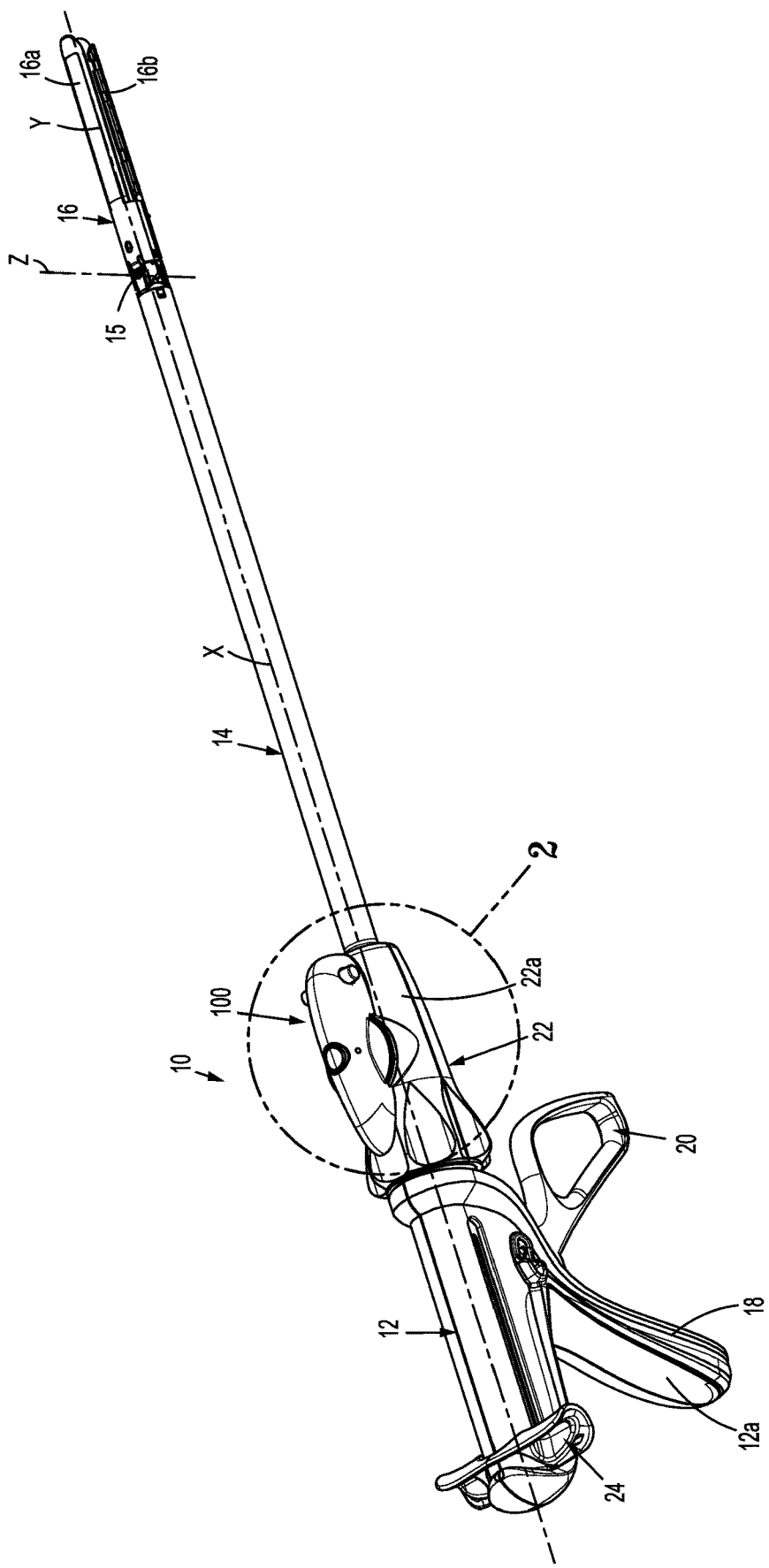
FIG. 1 is a side perspective view of a surgical stapling device according to aspects of the disclosure with the surgical stapling device in a non-articulated, clamped position.

The disclosed surgical device including exemplary aspects of the disclosed articulation assembly will now be described in detail with reference to the drawings in which like reference numerals designate identical or corresponding elements in each of the several views. However, it is to be understood that the aspects of the disclosure included herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, surgeons, and support personnel. Further, directional terms such as front, rear, upper, lower, top, bottom, and similar terms are used to assist in understanding the description and are not intended to limit the disclosure.

This disclosure is directed to a surgical device including an elongate body, a tool assembly supported on the elongate body for articulation, and an articulation assembly for selectively articulating the tool assembly in relation to the elongate body. The articulation assembly includes an articulation lever and a pair of locking assemblies. The articulation lever is movable to articulate the tool assembly in relation to the elongate body about an articulation axis. The locking assemblies prevent movement of the articulation lever until one of the locking assemblies is moved from a locked position to an unlocked position. The locking assemblies are movable from their locked positions to their unlocked positions prior to movement of the articulation lever to reduce the force required to manipulate the articulation lever and to facilitate articulation of the tool assembly in continuous fashion.

Figure 12:
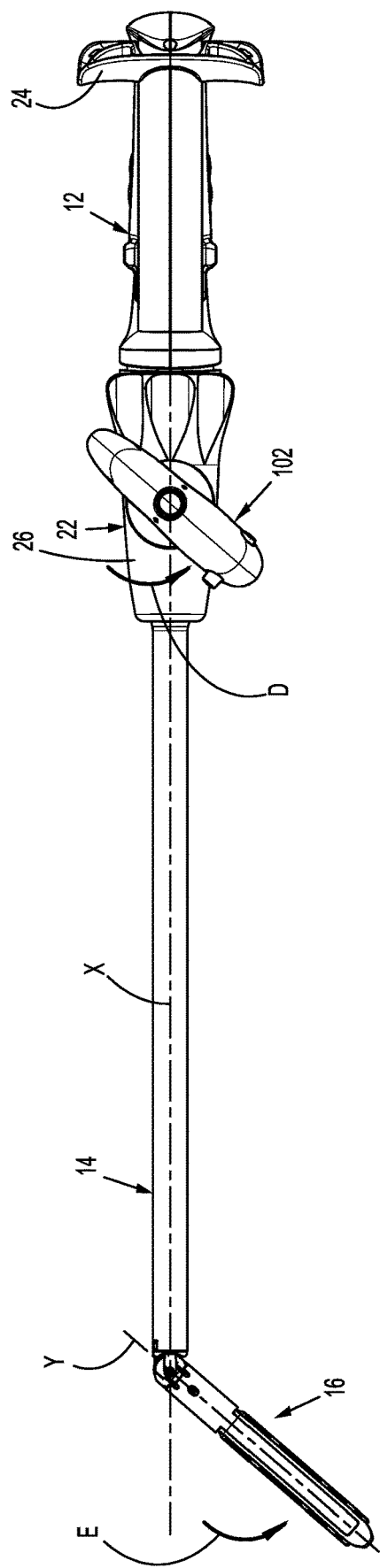
FIG. 12 is a perspective view from above of the surgical stapling device shown in FIG. 1 in an articulated position.

FIG. 1 illustrates a surgical device shown in the form of a stapling device 10 that includes a handle assembly 12, an elongate body or adapter assembly 14, and a tool assembly 16. As illustrated, the handle assembly 12 is manually actuated and includes a stationary handgrip 18, a firing trigger 20, a rotation knob 22, and a retraction knob 24. The handle assembly 12 supports the elongate body 14 and includes a body 12a that defines the stationary handgrip 18. The firing trigger 20 is movable in relation to the stationary handgrip 18 to actuate various functions of the tool assembly 16 via the elongate body 14 including approximation, stapling, and cutting. The handle assembly 12 supports the rotation knob 22 in a manner to facilitate rotation of the rotation knob 22 in relation to the handle assembly 12. The rotation knob 22 supports the elongate body 14 such that rotation of the rotation knob 22 in relation to the handle assembly 12 rotates the elongate body 14 and the tool assembly 16 in relation to the handle assembly 12 about a longitudinal axis "X" defined by the elongate body 14. The rotation knob 22 includes a body 23 that supports an articulation assembly 100 including an articulation lever 102 that is rotatable to articulate the tool assembly 16 as described in further detail below. The tool assembly 16 defines a longitudinal axis "Y-Y" (FIG. 26). The tool assembly 16 is pivotally coupled to the elongate body 14 about a pivot member 15 that defines an articulation axis "Z" to articulate between a non-articulated position in which the longitudinal axes "X" and "Y" of the elongate body 14 and tool assembly 16 are aligned with each other (FIG. 1) and articulated positions in which the longitudinal axes "X" and "Y" of the elongate body 14 and tool assembly 16 are offset from each other (FIG. 12).

The tool assembly 16 is illustrated to be a stapling device and includes an anvil 16a and a cartridge assembly 16b. It is envisioned that the articulation assembly 100 according to aspects of this disclosure could be incorporated into a variety of different endoscopic surgical devices including but not limited to clip appliers, ligation devices, vessel sealing devices, and graspers.

Figure 2:
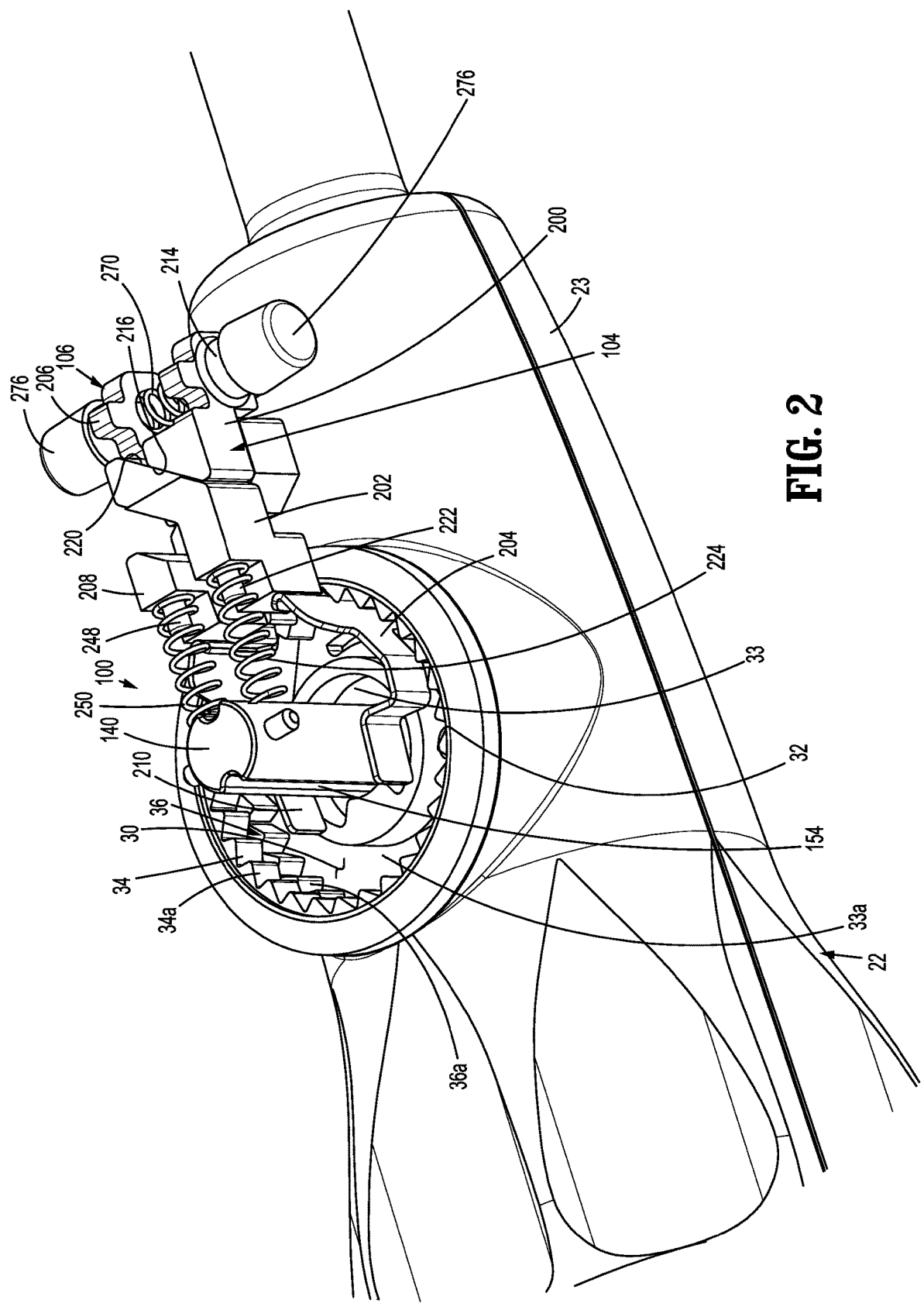
FIG. 2 is an enlarged view of the indicated area of detail shown in FIG. 1 showing an articulation assembly of the surgical stapling device with a lever of the articulation assembly removed.
Figure 3:
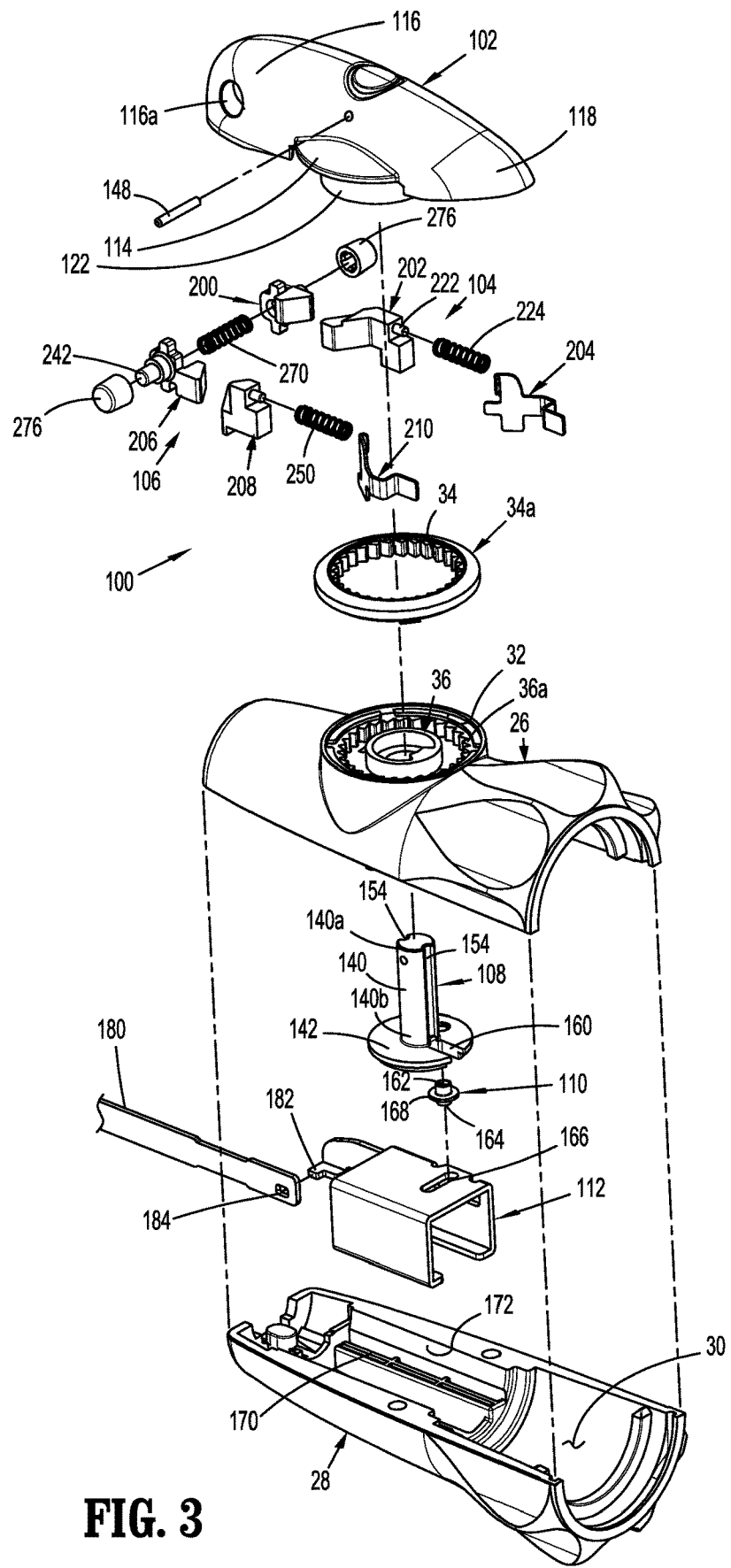
FIG. 3 is an exploded perspective view of the articulation assembly shown in FIG. 2.
Figure 3A:
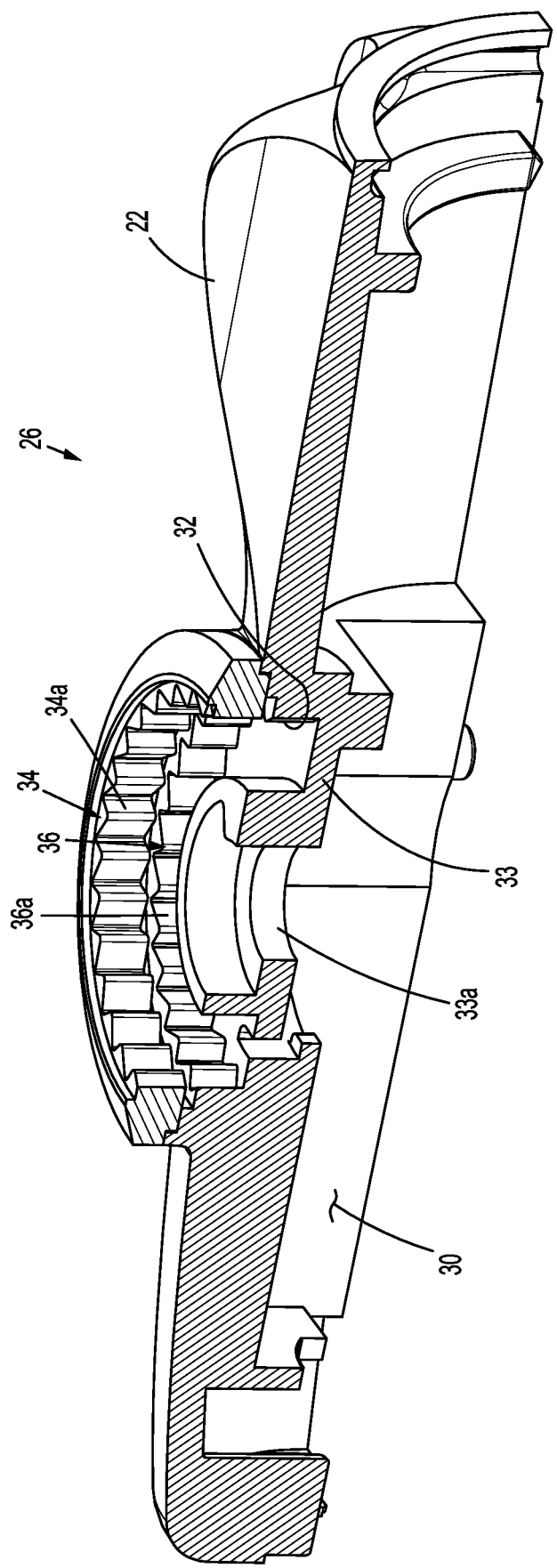
FIG. 3A is a cross-sectional view taken through a first body half-section of a rotation knob of the surgical stapling device shown in FIG. 1.
Figure 3B:
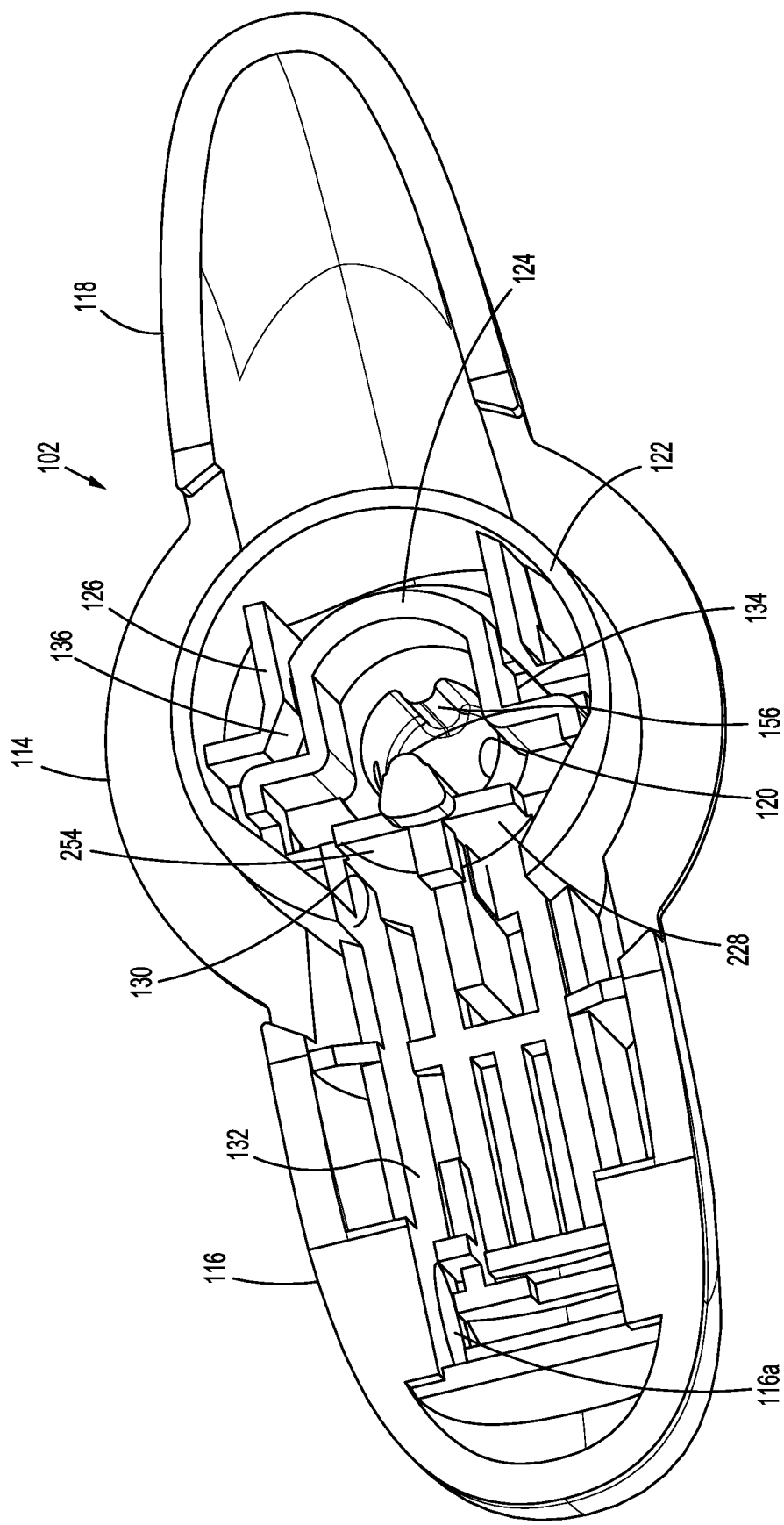
FIG. 3B is a perspective view from below of an articulation lever of the articulation assembly shown in FIG. 3.
Figure 4:
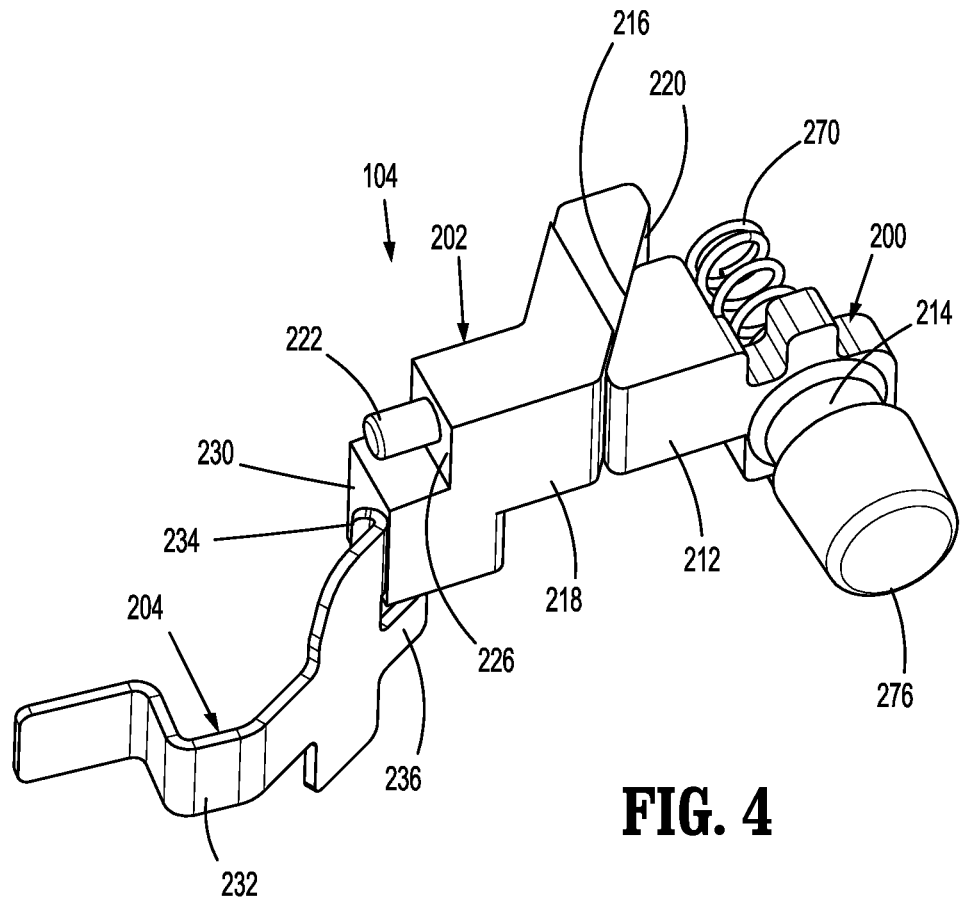
FIG. 4 is a side perspective view of a first locking assembly of the articulation assembly shown in FIG. 3.
Figure 5:
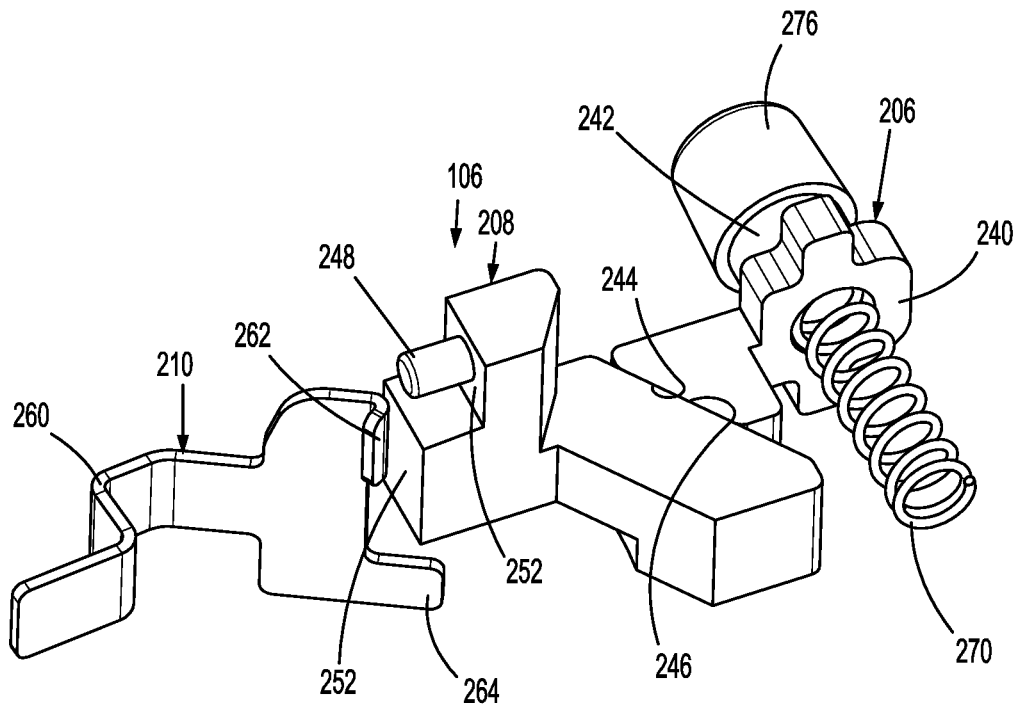
FIG. 5 is a side perspective view of a second locking assembly of the articulation assembly shown in FIG. 3.
Figure 6:
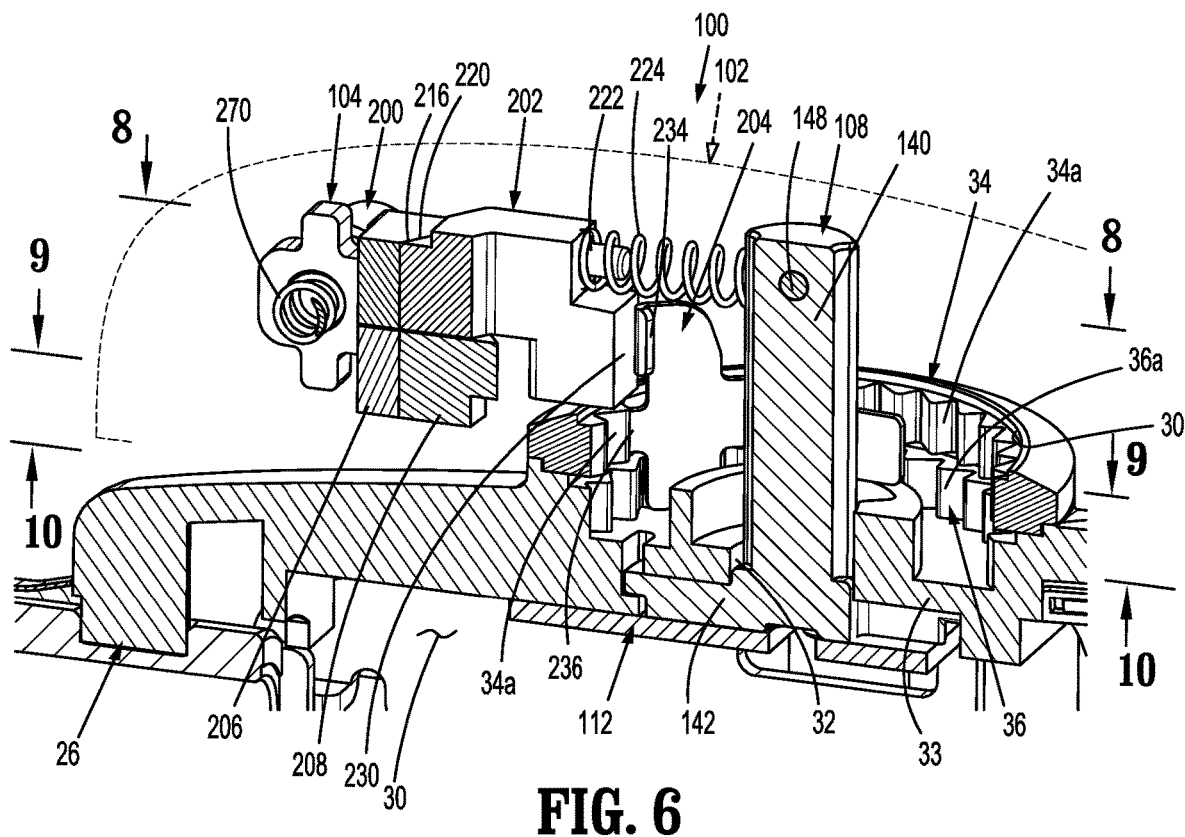
FIG. 6 is a cross-sectional view taken through the first locking assembly of the articulation assembly shown in FIG. 2 with the articulation lever shown in phantom.
Figure 7:
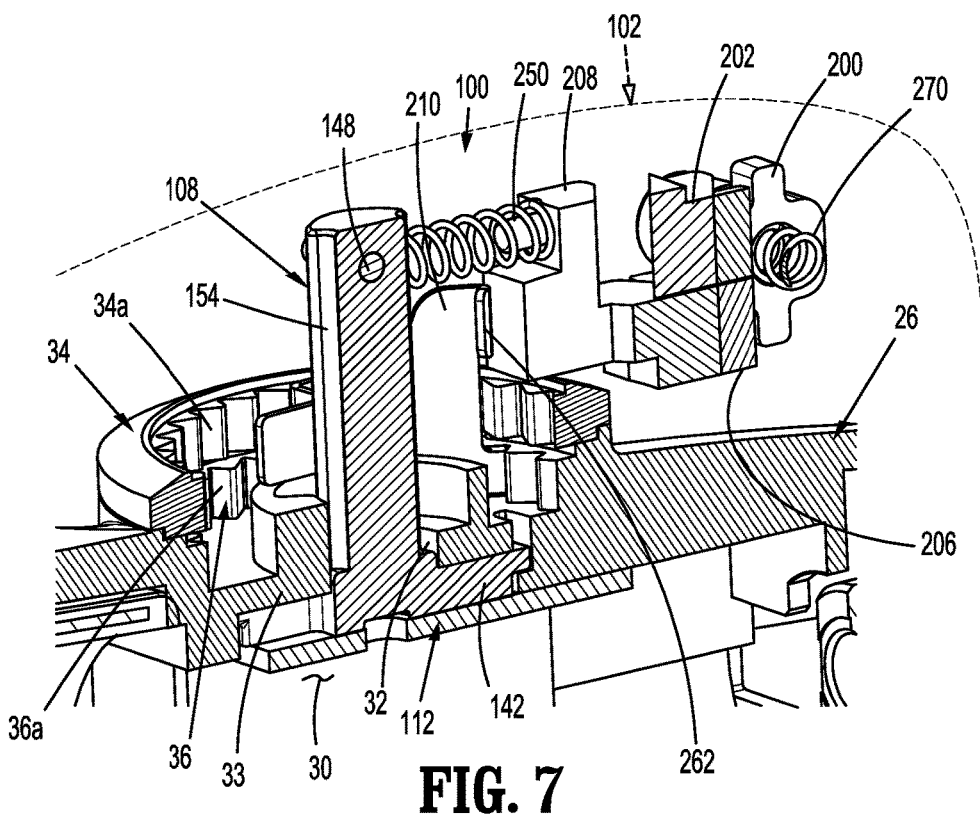
FIG. 7 is a cross-sectional view taken through the second locking assembly of the articulation assembly shown in FIG. 2 with the lever shown in phantom.
Figure 8:
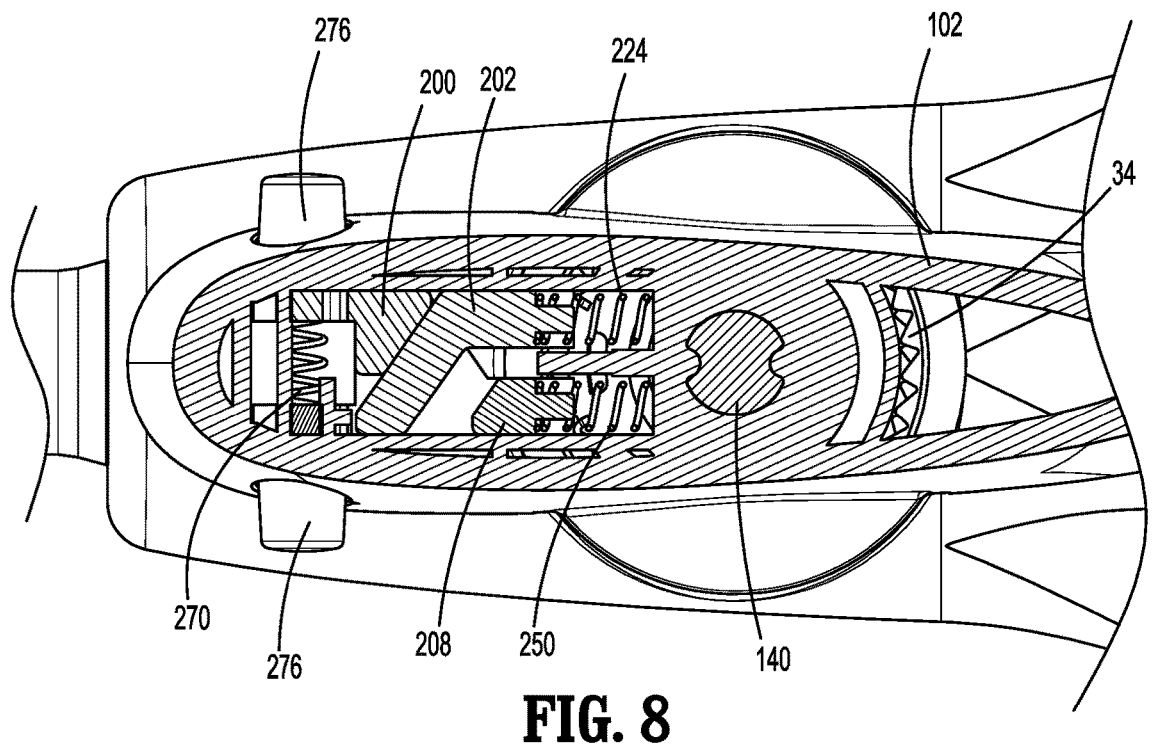
FIG. 8 is a cross-sectional view taken along section line 8-8 of FIG. 6.
Figure 9:
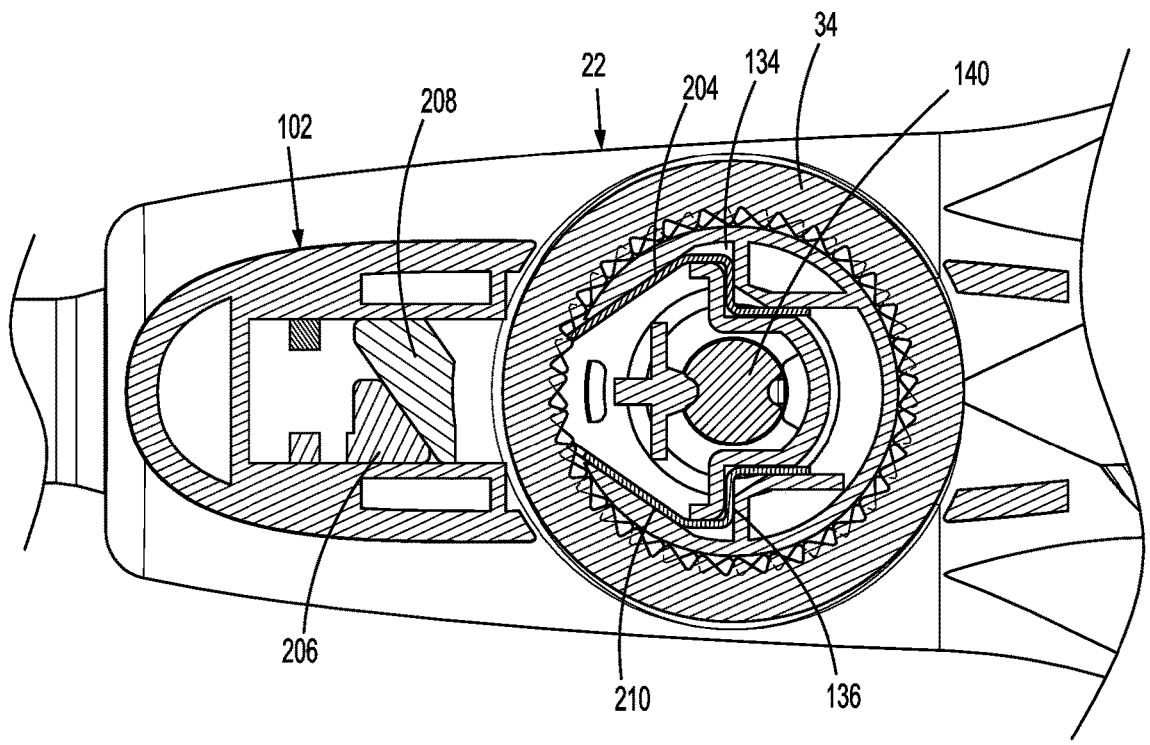
FIG. 9 is a cross-sectional view taken along section line 9-9 of FIG. 6.
Figure 10:
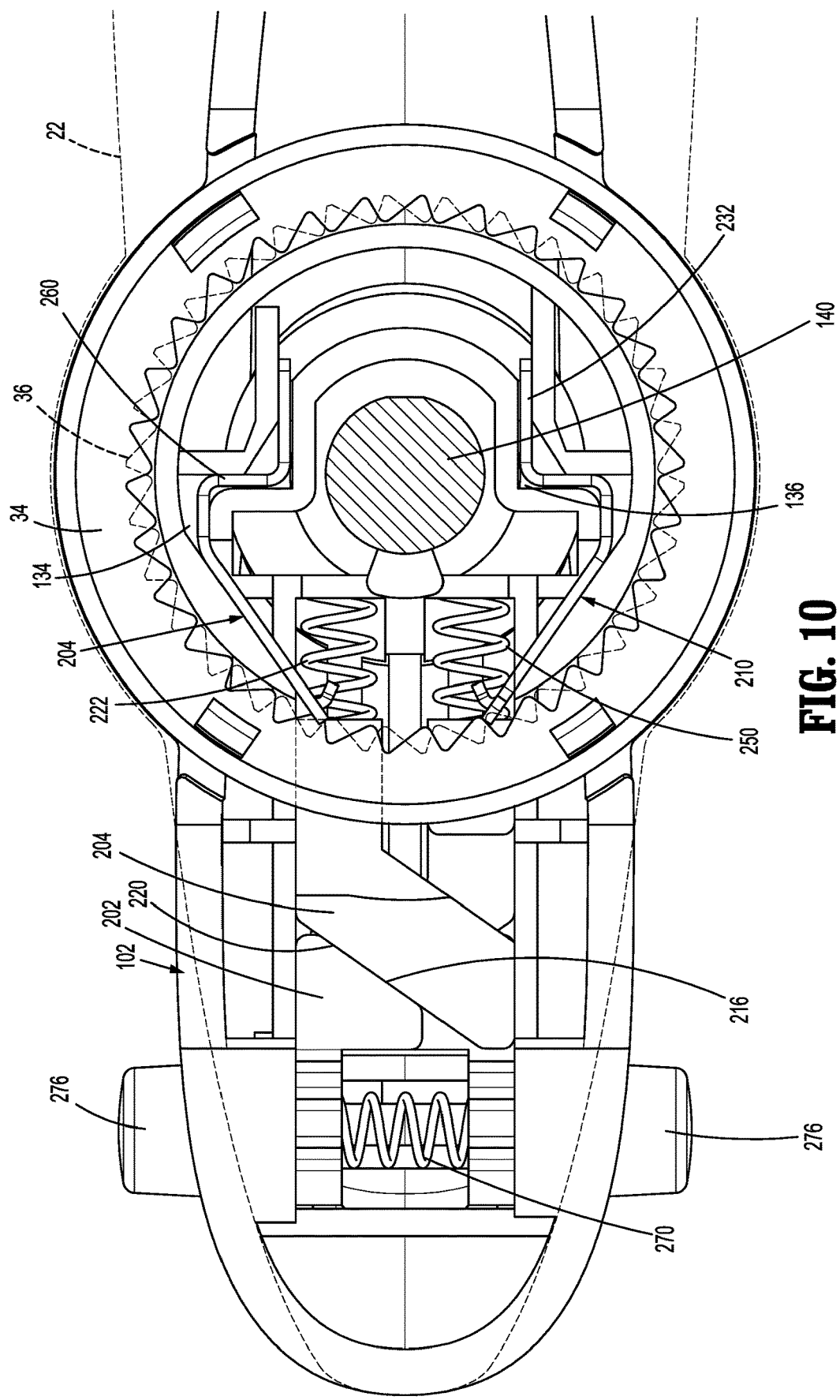
FIG. 10 is a cross-sectional view taken along section line 10-10 of FIG. 6.

FIGS. 2-3B illustrate the articulation assembly 100 of the stapling device 10 (FIG. 1) which is supported on and within the body 23 of the rotation knob 22. It is envisioned that the articulation assembly 100 need not be supported on the rotation knob but could be supported on a stationary housing of the stapling device 10. In aspects of the disclosure, the body 23 of the rotation knob 22 includes first and second body half-sections 26 and 28 that are secured together to define a cavity 30. The first body half-section 26 defines a circular bore 32 that receives the articulation assembly 100. The circular bore 32 is separated from the cavity 30 by a base wall 33 (FIG. 3A) that defines an opening 33a that extends between the circular bore 32 and the cavity 30. An upper end of the first body half-section 26 defining the circular bore 32 includes or supports a first ratchet 34 and a second ratchet 36. The first ratchet 34 has an annular array of ratchet teeth 34a and the second ratchet 36 has an annular array of ratchet teeth 36a. It is envisioned that the first and second ratchets 34 and 36 could be formed as a single ratchet member. In aspects of the disclosure, the second ratchet 36 has a circular configuration and is integrally formed with the first body half-section 26 and the first ratchet 34 has a circular configuration and is secured to the first body half-section 26 using known fastening techniques or devices, e.g., adhesives, welding, snap-connectors, or combinations thereof. It is envisioned that one or both first and second ratchets 34 and 36 can be integrally formed with the first body half-section 26 or formed separately from and secured to the first body half-section 26. As described in further detail below, the ratchet teeth 34a of the first ratchet 34 are angled in a direction to allow operation of the articulation assembly 100 only in a first direction, e.g., clockwise direction, and the ratchet teeth 36a of the second ratchet 36 are angled to allow operation of the articulation assembly 100 only in a second direction, e.g., counterclockwise direction.

The articulation assembly 100 includes the articulation lever 102, first and second locking assemblies 104 and 106, respectively, a drive member 108, a cam member 110, and a coupling member 112. The articulation lever 102 includes a central hub portion 114, a first extension 116, and a second extension 118. In aspects of the disclosure, the first and second extensions 116 and 118, respectively, are axially aligned with each other and extend outwardly from the central hub portion 114. In certain aspects of the disclosure, the first extension 116 extends distally from the central hub portion 114 and the second extension 118 extends proximally from the central hub portion 114. The first extension 116 defines a transverse through bore 116a. The central hub portion 114 of the articulation lever 102 defines a through bore 120 and includes an outer cylindrical wall 122, an inner retention wall 124, and outer retention walls 126 and 128. The outer cylindrical wall 122 is received within the circular bore 32 of the first body half-section 26 of the rotation knob 22 and defines a cutout 130 that is aligned with a channel 132 defined in the first extension 116 of the articulation lever 102. The channel 132 defined by the first extension 116 communicates with the transverse through bore 116a in the articulation lever 102.

The outer retention walls 126 and 128 are positioned on opposite sides of the inner guide wall 124. In aspects of the disclosure, the outer retention wall 126 and the inner retention wall 124 define a first stepped retention channel 134 on one side of the outer retention wall 124, and the inner retention wall 128 and the outer retention wall 124 define a second stepped retention channel 136 on the other side of the outer retention wall 124. The retention channels 134 and 136 are configured to help to secure the first and second locking assemblies 104 and 106 to the articulation lever 102 as described in further detail below. Other retention channel configurations are envisioned.

The drive member 108 of the articulation assembly 100 includes a central shaft 140 and a disc-shaped member 142. The central shaft 140 extends outwardly of the circular bore 32 in the rotation knob 22 and includes a first end portion 140a that is received within the through bore 120 (FIG. 3B) in the central hub portion 114 of the articulation lever 102 and a second end portion 140b that is fixedly secured to the disc-shaped member 142 within the cavity 30 of the rotation knob 22. The central shaft 140 of the drive member 108 extends through the opening 33a in the base wall 33 of the first body half-section 26 of the rotation knob 22 such that rotation of the articulation lever 102 externally of the cavity 30 of the rotation knob 22 causes corresponding rotation of the central shaft 140 and of the disc-shaped member 142 within the cavity 30. In aspects of the disclosure, the first end portion 140a of the central shaft 140 of the drive member 108 is secured to the articulation lever 102 by a pin 148 that extends through openings 150 and 152 formed in the articulation lever 102 and the central shaft 140, respectively. In certain aspects of the disclosure, the central shaft 140 of the drive member 108 defines elongate grooves 154 that receive protrusions 156 (FIG. 3B) formed within the central hub portion 114 of the articulation lever 102 to rotatably fix the articulation lever 102 to the drive member 108.

The disc-shaped member 142 of the drive member 108 can be integrally formed with the central shaft 140 or secured to the central shaft 140 using known fastening techniques or devices. The disc-shaped member 142 defines a radially extending slot 160 that extends from the central shaft 140 through an outer edge of the disc-shaped member 142.

The cam member 110 is received between the disc-shaped member 142 of the drive member 108 and the coupling member 112 and includes a first camming portion 162 (FIG. 3) and a second camming portion 164. The first camming portion 162 is slidably received within the radially extending slot 160 of the disc-shaped member 142 of the drive member 108 and the second camming portion 164 of the cam member 110 is received in a transverse slot 166 formed in the coupling member 112. In aspects of the disclosure, the camming member 110 includes a central flange 168 that has a diameter that is greater than the width of the transverse slot 166 of the coupling member 112 such that the cam member 110 can slide atop the coupling member 112 along the transverse slot 166 as the drive member 108 is rotated.

In aspects of the disclosure, the coupling member 112 has a rectangular configuration and is supported on shoulders 170 (only one is shown) within a channel 172 (FIG. 3) defined by the second body half-section 28 of the rotation knob 22. The channel 172 is dimensioned to restrict the coupling member 112 to longitudinal movement within the rotation knob 22. When the articulation lever 102 is rotated to rotate the drive member 108, the disc-shaped member 142 of the drive member 108 rotates to move the cam member 110 over a circular path of movement that includes transverse and longitudinal components. As the cam member 110 moves along the circular path of movement, the longitudinal component of movement of the cam member 110 is translated to longitudinal movement of the coupling member 112 within the channel 172 of the rotation knob 22.

The coupling member 112 includes a connector 178 that is coupled to an articulation link 180 (FIG. 3) of the stapling device 10 (FIG. 1). The articulation link 180 includes a distal portion (not shown) that is coupled to the tool assembly 16 such that longitudinal movement of the articulation link 180 causes the tool assembly (FIG. 1) to articulate about the articulation axis "Z" (FIG. 1). In aspects of the disclosure, the connector 178 includes a transversely extending finger 182 that extends through an opening 184 in a proximal portion of the articulation link 180. It is envisioned that a variety of different connector configurations can be used to couple the coupling member 112 to the articulation link 180. For a more detailed description of the construction and operation of a suitable articulation link, see U.S. Pat. No. 7,891,534.

FIGS. 3-7 illustrate the first and second locking assemblies 104 and 106 which are supported within the channel 132 of the articulation lever 102 and extend into circular bore 32 (FIG. 2) defined by the first body half-section 26 of the rotation knob 22. The first locking assembly 104 (FIG. 4) includes an actuator 200, a slider 202, and a locking member 204. Similarly, the second locking assembly 106 (FIG. 5) includes an actuator 206, a slider 208, and a locking member 210. The first and second locking assemblies 104 and 106 are substantially similar in construction and operate in substantially the same manner.

The actuator 200 includes a body 212 (FIG. 4) that has a transversely extending post 214 and an angled cam surface 216. The transversely extending post 214 extends through one side of the transverse through bore 116a (FIG. 3) in the articulation lever 102 and can be pressed inwardly from a non-depressed position to a depressed position into the through bore 116a of the articulation lever 102 to move the body 212 of the actuator 200 inwardly into the channel 132 of the articulation lever 102.

The slider 202 is slidably supported within the channel 132 of the articulation lever 102 and includes an angled cam surface 220 that is in abutting relation with the angled cam surface 216 of the actuator 200. The angled cam surfaces 216 and 220 are configured such that when the actuator 200 is pressed inwardly into the channel 132 of the articulation lever 102, the slider 202 is moved longitudinally in a direction towards the circular bore 32 (FIG. 3) of the rotation knob 22 from a first position towards a second position. The slider 202 includes a post 222 that supports a biasing member, e.g., a coil spring 224, that is positioned to urge the slider 202 towards its first position. In aspects of the disclosure, the coil spring 224 is positioned in compression about the post 222 between a surface 226 of the slider 202

(FIG. 4) and an inner wall 228 (FIG. 3B) of the articulation lever 102. The slider 202 also includes an engagement surface 230.

The locking member 204 is formed of a resilient material, e.g., spring steel, and includes a retention portion 232, an abutment portion 234, and a ratchet finger 236. The retention portion 232 of the locking member 204 is secured within the retention channel 134 (FIG. 3B) of the articulation lever 102. In aspects of the disclosure, the retention portion 232 of the locking member 204 has a stepped configuration that corresponds to the configuration of the retention channel 134. When the articulation lever 102 is secured to the central shaft 140 of the drive member 108 and the slider 202 is in its first position, the ratchet finger 236 of the locking member 204 engages a tooth 34a of the first ratchet 34 (FIG. 3) to limit rotation of the articulation lever 102 to one direction, e.g., a clockwise direction. The ratchet finger 236 is formed of a resilient material that is configured to flex or ratchet over the teeth 34a when the articulation lever 102 is rotated in the permitted direction. Rotation of the articulation lever 102 in the opposite direction, e.g., the counter-clockwise direction, is prevented by the engagement of the ratchet finger 236 with one of the teeth 34a of the first ratchet 34.

The abutment portion 234 of the locking member 204 is engaged with the engagement surface 230 of the slider 202. When the slider 202 is moved from its first position to its second position by pressing the actuator 200 into the channel 132 (FIG. 3B) of the articulation lever 102, the locking member 204 is deformed to disengage the ratchet finger 236 from the first ratchet 34 and, thus allow rotation of the articulation lever 102 in both directions.

The actuator 206 includes a body 240 (FIG. 4) that has a transversely extending post 242 and an angled cam surface 244. The transversely extending post 242 extends through the other side of the transverse through bore 116a (FIG. 3) in the articulation lever 102 and can be pressed inwardly into the through bore 116a from a non-depressed position to a depressed position to move the body 240 of the actuator 206 inwardly into the channel 132 of the articulation lever 102.

The slider 208 of the second locking assembly 106 is slidably supported within the channel 132 (FIG. 3B) of the articulation lever 102 and includes an angled cam surface 246 that is in abutting relation with the angled cam surface 244 of the actuator 206. The angled cam surfaces 244 and 246 are configured such that when the actuator 206 is pressed inwardly into the channel 132 (FIG. 3B) of the articulation lever 102, the slider 208 is moved longitudinally in a direction towards the circular bore 32 (FIG. 3) of the rotation knob 22 from a first position towards a second position. The slider 208 includes a post 248 that supports a biasing member, e.g., a coil spring 250, that is positioned to urge the slider 208 towards its first position. In aspects of the disclosure, the coil spring 250 is positioned in compression about the post 248 between a surface 252 of the slider 208 (FIG. 5) and an inner wall 254 (FIG. 3B) of the articulation lever 102. The slider 208 also includes an engagement surface 256.

The locking member 210 is formed of a resilient material, e.g., spring steel, and includes a retention portion 260, an abutment portion 262, and a ratchet finger 264. The retention portion 260 of the locking member 210 is secured within the retention channel 136 (FIG. 3B) of the articulation lever 102. In aspects of the disclosure, the retention portion 260 of the locking member 210 has a stepped configuration that corresponds to the configuration of the retention channel 136. When the articulation lever 102 is secured to the central shaft 140 of the drive member 108 and the slider 208 is in its first position, the ratchet finger 264 of the locking member 210 engages a tooth 36a of the second ratchet 36 (FIG. 3) to limit rotation of the articulation lever 102 to one direction, e.g., a counterclockwise direction. The ratchet finger 264 is formed of a resilient material and is configured to flex or ratchet over the teeth 36a when the articulation lever 102 is rotated in the permitted direction. Rotation of the articulation lever 102 in the opposite direction, e.g., the clockwise direction, is prevented by the engagement of the ratchet finger 264 with the second ratchet 36.

The abutment portion 262 of the locking member 210 is engaged with the engagement surface 252 of the slider 208. When the slider 208 is moved from its first position to its second position by pressing the actuator 206 into the channel 132 (FIG. 3B) of the articulation lever 102, the locking member 210 is deformed to disengage the ratchet finger 264 from the second ratchet 36 and, thus allow rotation of the articulation lever 102 in both directions.

In aspects of the disclosure, each of the actuators 200 and 206 of the first and second locking assemblies 104 and 106, respectively, defines a bore 200a (FIG. 3) and 206a (FIG. 5) that receives a biasing member, e.g., a coil spring 270. The coil spring 270 is positioned between the actuators 200 and 206 to urge the actuators 200 and 206 to their non-depressed positions. In certain aspects of the disclosure, the posts 214 and 242 of actuators 200 and 206 include a cover or cap 276. The caps 276 can be formed of a soft material such as rubber to facilitate more comfortable depression of the actuators 200 and 206 by a clinician.

FIGS. 6-10 illustrate the articulation assembly 100 in a locked position. In the locked position, the actuators 200 and 206 of the first and second locking assemblies 104 and 106 are in non-depressed positions and the sliders 202 and 208 are in their first positions. More specifically, the coil spring 270 urges the actuators 200 and 206 of the first and second locking assemblies 104 and 106 to their non-depressed positions, and the coil springs 224 and 250 urge the sliders 202 and 208, respectively, to their first positions. In the first positions of the sliders 202 and 208, the ratchet finger 236 of the locking member 204 is engaged with a tooth 34a of the first ratchet 34 to prevent rotation of the articulation lever 102 in a counterclockwise direction and the ratchet finger 264 of the locking member 210 is engaged with a tooth 36a of the second ratchet 36 to prevent rotation of the articulation lever 102 in a clockwise direction. In this position, the articulation assembly 100 is locked out such that the articulation lever 102 cannot be rotated in either direction.

Figure 11:
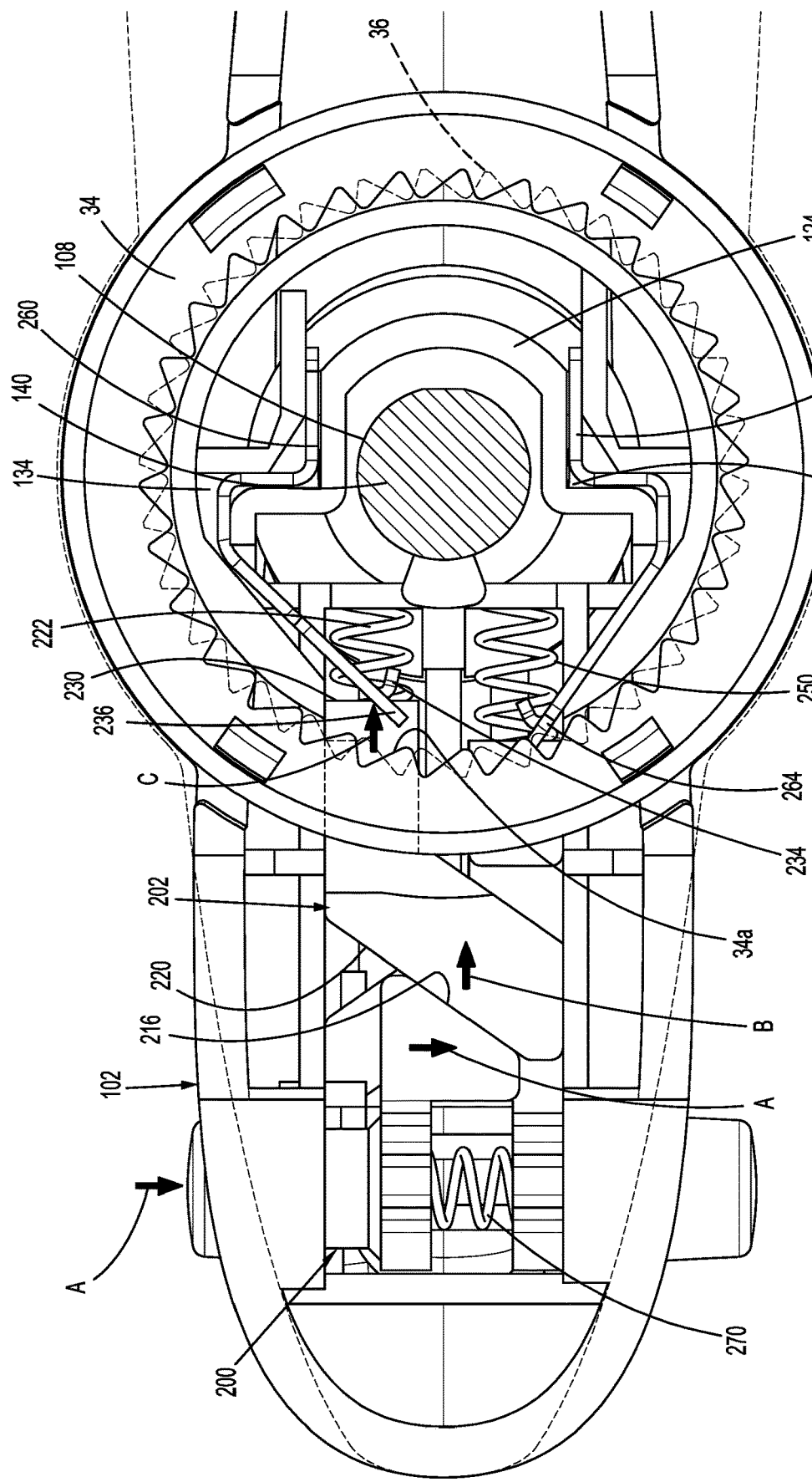
FIG. 11 is a top view of the articulation assembly shown in FIG. 2 with the first locking assembly actuated and in an unlocked position.

FIGS. 11 and 12 illustrate the articulation assembly 100 when the first locking assembly 104 is unlocked and the articulation lever 102 is rotated in a counterclockwise direction to articulate the tool assembly 16 about the articulation axis "Z" (FIG. 1). When the actuator 200 is depressed in the direction of arrows "A" in FIG. 11 to depress the coil spring 270, the cam surface 216 of the actuator 200 engages the cam surface 220 of the slider 202 to move the slider 202 in the direction of arrow "B" in FIG. 11. When the slider 202 moves in the direction of arrow "B", the engagement surface 230 on the slider 202 engages the abutment portion 234 of the locking member 204 to deform the locking member 204 inwardly in the direction of arrow "C" to disengage the ratchet finger 236 from the tooth 34a of the first ratchet 34. Once the ratchet finger 236 is disengaged from the first ratchet 34, the articulation lever 102 of the articulation assembly 100 can be rotated in a counterclockwise direction as indicated by arrow "D" in FIG. 12 to articulate the tool assembly 16 in the direction of arrow "E" in FIG. 12 about the articulation axis "Z" (FIG. 1). Operation of the second locking assembly 106 to articulate the tool assembly 16 in the clockwise direction is identical to operation of the first locking assembly 104 described above and will not be described in further detail herein.

It is noted that when the actuator 200 is depressed to unlock the first locking assembly 104, the second locking assembly 106 remains in a locked position to prevent movement of the articulation lever 102 in a clockwise direction. It is envisioned that both actuators 200 and 206 could be simultaneously depressed to simultaneously unlock the first and second locking assemblies 104 and 106 to facilitate selective movement of the articulation lever 102 in either direction.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An articulation assembly for use with a surgical device comprising:
    a housing defining a circular bore and a cavity and including a base wall separating the circular bore from the cavity, the base wall defining an opening that communicates the circular bore with the cavity;
    an articulation lever rotatably supported in relation to the circular bore;
    a first ratchet having an annular array of teeth supported within the circular bore;
    a second ratchet having an annular array of teeth positioned adjacent the first ratchet;
    a drive member including a shaft having a first end coupled to the articulation lever and a second end, the shaft extending through the opening in the base wall of the housing, and the drive member rotatable in response to rotation of the articulation lever;
    an articulation link coupled to the second end of the drive member such that rotation of the drive member causes longitudinal movement of the articulation link;
    a first locking assembly supported on the articulation lever, the first locking assembly comprising:
        a first locking member that is movable from a ratchet engaged position, engaged with the first ratchet, to a ratchet disengaged position disengaged with the first ratchet, with the first locking member preventing rotation of the articulation lever in a counterclockwise direction when the first locking member is in the ratchet engaged position;
        a first actuator supported on the articulation lever and movable from a first position to a second position; and
        a first slider positioned between the first actuator and the first locking member and movable from a disengaged position, disengaged from the first locking member, to an engaged position engaging the first locking member;
        wherein motion of the first actuator from the first position to the second position moves the first slider from the disengaged position to the engaged position; and
        wherein engagement of the first slider with the first locking member drives the first locking member into the ratchet engaged position to prevent counterclockwise rotation of the articulation lever; and
    a second locking assembly supported on the articulation lever, the second locking assembly comprising:
        a second locking member that is movable from a ratchet engaged position engaged with the second ratchet to a ratchet disengaged position disengaged with the second ratchet, with the second locking member preventing rotation of the articulation lever in a clockwise direction when the second locking member is in the ratchet engaged position;
        a second actuator supported on the articulation lever and movable from a first position to a second position; and
        a second slider positioned between the second actuator and the second locking member and movable from a disengaged position, disengaged from the second locking member, to an engaged position engaging the second locking member;
        wherein motion of the second actuator from the first position to the second position moves the second slider from the disengaged position to the engaged position; and
        wherein engagement of the second slider with the second locking member drives the second locking member into the ratchet engaged position to prevent clockwise rotation of the articulation lever.

2. The articulation assembly of claim 1, wherein the first actuator and the first slider include abutting cam surfaces such that transverse movement of the first actuator causes longitudinal movement of the first slider, and wherein the second actuator and the second slider include abutting cam surfaces such that transverse movement of the second actuator causes longitudinal movement of the second slider.

3. The articulation assembly of claim 2, further including a biasing member positioned to urge the first and second actuators towards their corresponding engaged positions.

4. The articulation assembly of claim 2, wherein the first and second locking members are formed of a resilient material, the first locking member including a first retention portion and a first ratchet finger, and the second locking member including a second retention portion and a second ratchet finger, the first ratchet finger engaged with the first ratchet when the first locking member is in its ratchet engaged position and the second ratchet finger engaged with the second ratchet when the second locking member is in its ratchet engaged position.

5. The articulation assembly of claim 4, further including a first biasing member positioned to urge the first slider to its engaged position and a second biasing member positioned to urge the second slider to its engaged position.

6. The articulation assembly of claim 1, wherein the second end of the drive member includes a disc-shaped member, and the articulation assembly further includes a cam member and a coupling member, the cam member supported on the disc-shaped member and coupled to the coupling member such that rotational movement of the drive member causes longitudinal movement of the coupling member.

7. The articulation assembly of claim 6, wherein the coupling member is coupled to the articulation link such that longitudinal movement of the coupling member causes longitudinal movement of the articulation link.

8. A surgical device comprising:
an elongate body defining a first longitudinal axis and having a proximal portion and a distal portion;
a tool assembly defining a second longitudinal axis, the tool assembly pivotably supported on the distal portion of the elongate body by a pivot member, the pivot member defining an articulation axis that is transverse to the first longitudinal axis, the tool assembly being pivotable about the articulation axis in relation to the elongate body between a non-articulated position, in which the first and second longitudinal axes are coaxial, and an articulated position in which the first and second longitudinal axes are misaligned; and
an articulation assembly including:
a housing defining a circular bore and a cavity and including a base wall separating the circular bore from the cavity, the base wall defining an opening that communicates the circular bore with the cavity;
an articulation lever rotatably supported in relation to the circular bore;
a first ratchet having an annular array of teeth supported within the circular bore;
a second ratchet having an annular array of teeth supported adjacent the first ratchet;
a drive member including a shaft having a first end coupled to the articulation lever and a second end, the shaft extending through the opening in the base wall of the housing, and the drive member rotatable in response to rotation of the articulation lever;
an articulation link having a proximal portion and a distal portion, the proximal portion coupled to the second end of the drive member such that rotation of the drive member causes longitudinal movement of the articulation link, the distal portion of the articulation link coupled to the tool assembly such that longitudinal movement of the articulation link causes the tool assembly to move between the non-articulated and articulated positions;
a first locking assembly supported on the articulation lever, the first locking assembly comprising:
a first locking member that is movable from a ratchet engaged position engaged with the first ratchet to a ratchet disengaged position disengaged with the first ratchet, with the first locking member preventing rotation of the articulation lever in a counterclockwise direction when the first locking member is in the ratchet engaged position;
a first actuator supported on the articulation lever and movable from a first position to a second position; and
a first slider positioned between the first actuator and the first locking member and movable from a disengaged position, disengaged from the first locking member, to an engaged position engaging the first locking member;
wherein motion of the first actuator from the first position to the second position moves the first slider from the disengaged position to the engaged position; and
a second locking assembly supported on the articulation lever, the second locking assembly comprising:
a second locking member that is movable from a ratchet engaged position engaged with the second ratchet to a ratchet disengaged position disengaged with the second ratchet, with the second locking member preventing rotation of the articulation lever in a clockwise direction when the second locking member is in the ratchet engaged position;
a second actuator supported on the articulation lever and movable from a first position to a second position; and
a second slider positioned between the second actuator and the second locking member and movable from a disengaged position, disengaged from the second locking member, to an engaged position engaging the second locking member;
wherein motion of the second actuator from the first position moves the second slider from the disengaged position to the engaged position; and
wherein engagement of the second slider with the second locking member drives the second locking member into the ratchet engaged position to prevent clockwise rotation of the articulation lever.

9. The surgical device of claim 8, wherein the first actuator and the first slider include abutting cam surfaces such that transverse movement of the first actuator causes longitudinal movement of the first slider, and wherein the second actuator and the second slider include abutting cam surfaces such that transverse movement of the second actuator causes longitudinal movement of the second slider.

10. The surgical device of claim 9, further including a biasing member positioned to urge the first and second actuators towards their corresponding engaged positions.

11. The surgical device of claim 9, wherein the first and second locking members are formed of a resilient material, the first locking member including a first retention portion and a first ratchet finger, and the second locking member including a second retention portion and a second ratchet finger, the first ratchet finger engaged with the first ratchet when the first locking member is in its ratchet engaged position and the second ratchet finger engaged with the second ratchet when the second locking member is in its ratchet engaged position.

12. The surgical device of claim 11, further including a first biasing member positioned to urge the first slider to its engaged position and a second biasing member positioned to urge the second slider to its engaged position.

13. The surgical device of claim 8, wherein the second end of the drive member includes a disc-shaped member, and the articulation assembly further includes a cam member and a coupling member, the cam member supported on the disc-shaped member and coupled to the coupling member such that rotational movement of the drive member causes longitudinal movement of the coupling member.

14. The surgical device of claim 13, wherein the coupling member is coupled to the proximal portion of the articulation link such that longitudinal movement of the coupling member causes longitudinal movement of the articulation link.

15. The surgical device of claim 8, wherein the tool assembly includes an anvil and a cartridge assembly.

16. An articulation assembly for use with a surgical device comprising:
a housing defining a circular bore;
an articulation lever rotatably supported in relation to the circular bore;
a first ratchet having an annular array of teeth supported on the housing;
a second ratchet having an annular array of teeth positioned adjacent the first ratchet;

a drive member including a shaft having a first end coupled to the articulation lever;

a first locking assembly supported on the articulation lever, the first locking assembly comprising:
- a first locking member that is movable from a ratchet engaged position, engaged with the first ratchet, to a ratchet disengaged position disengaged with the first ratchet, with the first locking member preventing rotation of the articulation lever in a counterclockwise direction when the first locking member is in the ratchet engaged position;
- a first actuator supported on the articulation lever and movable from a first position to a second position; and
- a first slider positioned between the first actuator and the first locking member and movable from a disengaged position, disengaged from the first locking member, to an engaged position engaging the first locking member;
- wherein motion of the first actuator from the first position to the second position moves the first slider from the disengaged position to the engaged position; and
- wherein engagement of the first slider with the first locking member drives the first locking member into the ratchet engaged position to prevent counterclockwise rotation of the articulation lever; and a second locking assembly supported on the articulation lever, the second locking assembly comprising:
- a second locking member that is movable from a ratchet engaged position, engaged with the second ratchet, to a ratchet disengaged position disengaged with the second ratchet, with the second locking member preventing rotation of the articulation lever in a clockwise direction when the second locking member is in the ratchet engaged position;
- a second actuator supported on the articulation lever and movable from a first position to a second position; and
- a second slider positioned between the second actuator and the second locking member and movable from a disengaged position, disengaged from the second locking member, to an engaged position engaging the second locking member;
- wherein motion of the second actuator from the first position moves the second slider from the disengaged position to the engaged position; and
- wherein engagement of the second slider with the second locking member drives the second locking member into the ratchet engaged position to prevent clockwise rotation of the articulation lever.

* * * * *